(12) United States Patent
Baerveldt

(10) Patent No.: US 9,468,558 B2
(45) Date of Patent: Oct. 18, 2016

(54) GLAUCOMA DRAINAGE SHUNTS AND METHODS OF USE

(71) Applicant: Abbott Medical Optics Inc., Santa Ana, CA (US)

(72) Inventor: George Baerveldt, Monarch Beach, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 14/572,324

(22) Filed: Dec. 16, 2014

(65) Prior Publication Data

US 2015/0100010 A1 Apr. 9, 2015

Related U.S. Application Data

(62) Division of application No. 13/714,050, filed on Dec. 13, 2012, now Pat. No. 8,920,357, which is a division of application No. 12/265,145, filed on Nov. 5, 2008, now Pat. No. 8,353,856.

(51) Int. Cl.
*A61F 9/007* (2006.01)
*A61M 27/00* (2006.01)
*A61F 9/008* (2006.01)

(52) U.S. Cl.
CPC .......... *A61F 9/00781* (2013.01); *A61F 9/007* (2013.01); *A61M 27/002* (2013.01); *A61F 2009/00891* (2013.01); *A61M 2210/0612* (2013.01); *Y10S 623/905* (2013.01)

(58) Field of Classification Search
CPC ..................... A61F 2009/00891; A61F 9/007; A61F 9/00781; A61M 2210/0612; A61M 27/002; Y10S 623/905
See application file for complete search history.

(56) References Cited

U.S. PATENT DOCUMENTS

| 1,246,971 | A | 11/1917 | Maier |
| 2,969,066 | A | 1/1961 | Holter et al. |
| 3,109,429 | A | 11/1963 | Samuel |

(Continued)

FOREIGN PATENT DOCUMENTS

| EP | 102747 A1 | 3/1984 |
| EP | 168201 A1 | 1/1986 |

(Continued)

OTHER PUBLICATIONS

Bickford M.E., "Molteno Implant System, for Patient with Previously Unsuccessful Glaucoms Surgery," Journal of Ophthalmic Nursing & Technology, 1987, vol. 6 (6), pp. 224-229.

(Continued)

*Primary Examiner* — Adam Marcetich
(74) *Attorney, Agent, or Firm* — Abbott Medical Optics Inc.

(57) ABSTRACT

A method of treating glaucoma in an eye utilizing an implanted shunt having an elastomeric plate and a non-valved elastomeric drainage tube. The plate is positioned over a sclera of the eye with an outflow end of the elastomeric drainage tube open to an outer surface of the plate. An inflow end of the drainage tube tunnels through the sclera and cornea to the anterior chamber of the eye. The drainage tube collapses upon initial insertion within an incision in the sclera and cornea, or at a kink on the outside of the incision, but has sufficient resiliency to restore its patency over time. The effect is a flow restrictor that regulates outflow from the eye until a scar tissue bleb forms around the plate of the shunt.

2 Claims, 4 Drawing Sheets

(56) References Cited

U.S. PATENT DOCUMENTS

| | | |
|---|---|---|
| 3,159,161 A | 12/1964 | Alton |
| 3,527,226 A | 9/1970 | Salomon |
| 3,726,284 A | 4/1973 | Parker |
| 3,788,327 A | 1/1974 | Donowitz et al. |
| 3,860,008 A | 1/1975 | Miner et al. |
| 3,915,172 A | 10/1975 | Wichterle et al. |
| 4,030,480 A | 6/1977 | Meyer |
| 4,240,434 A | 12/1980 | Newkirk |
| 4,298,994 A | 11/1981 | Clayman |
| 4,373,218 A | 2/1983 | Schachar |
| 4,402,681 A | 9/1983 | Haas et al. |
| 4,428,746 A | 1/1984 | Mendez |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,634,418 A | 1/1987 | Binder |
| 4,722,724 A | 2/1988 | Schocket |
| 4,729,761 A | 3/1988 | White |
| 4,750,901 A | 6/1988 | Molteno |
| 4,767,400 A | 8/1988 | Miller et al. |
| 4,836,457 A | 6/1989 | Greiner |
| 4,863,457 A | 9/1989 | Lee |
| 4,865,601 A | 9/1989 | Caldwell et al. |
| 4,886,488 A | 12/1989 | White |
| 4,902,292 A | 2/1990 | Joseph |
| 4,915,684 A | 4/1990 | MacKeen et al. |
| 4,932,968 A | 6/1990 | Caldwell et al. |
| 4,936,825 A | 6/1990 | Ungerleider |
| 4,946,436 A | 8/1990 | Smith |
| 4,955,909 A | 9/1990 | Ersek et al. |
| 4,968,296 A | 11/1990 | Ritch et al. |
| 5,092,837 A | 3/1992 | Ritch et al. |
| 5,171,213 A | 12/1992 | Price |
| 5,178,604 A | 1/1993 | Baerveldt et al. |
| 5,192,315 A | 3/1993 | Jacob-LaBarre |
| 5,282,851 A | 2/1994 | Jacob-LaBarre |
| 5,300,020 A * | 4/1994 | L'Esperance, Jr. . A61F 9/00781 604/9 |
| 5,338,291 A | 8/1994 | Speckman et al. |
| 5,372,577 A | 12/1994 | Ungerleider |
| 5,397,300 A | 3/1995 | Baerveldt et al. |
| 5,476,445 A * | 12/1995 | Baerveldt ........... A61M 27/002 604/294 |
| 5,549,670 A | 8/1996 | Young et al. |
| 5,558,629 A * | 9/1996 | Baerveldt ........... A61M 27/002 604/540 |
| 5,704,907 A | 1/1998 | Nordquist et al. |
| 5,713,844 A | 2/1998 | Peyman |
| 5,725,493 A | 3/1998 | Avery et al. |
| 5,752,928 A | 5/1998 | de Roulhac et al. |
| 5,882,327 A | 3/1999 | Jacob |
| 6,007,510 A * | 12/1999 | Nigam ................ A61F 9/00781 604/8 |
| 6,050,970 A | 4/2000 | Baerveldt |
| 6,203,513 B1 | 3/2001 | Yaron et al. |
| 6,261,256 B1 | 7/2001 | Ahmed |
| 6,984,392 B2 | 1/2006 | Bechert et al. |
| 7,160,264 B2 | 1/2007 | Lisk et al. |
| 7,207,965 B2 | 4/2007 | Simon |
| 7,220,238 B2 | 5/2007 | Lynch et al. |
| 7,297,130 B2 | 11/2007 | Bergheim et al. |
| 7,357,778 B2 | 4/2008 | Bhalla |
| 7,476,698 B2 | 1/2009 | Wagener et al. |
| 7,547,302 B2 | 6/2009 | Porto et al. |
| 7,635,358 B2 | 12/2009 | Tan |
| 7,641,627 B2 | 1/2010 | Camras et al. |
| 8,353,856 B2 * | 1/2013 | Baerveldt ........... A61F 9/00781 604/10 |
| 8,920,357 B2 * | 12/2014 | Baerveldt ........... A61F 9/00781 604/289 |
| 2005/0125003 A1 | 6/2005 | Pinchuk et al. |
| 2005/0267398 A1 | 12/2005 | Protopsaltis et al. |
| 2006/0155300 A1 * | 7/2006 | Stamper ............... A61F 9/00781 606/107 |
| 2007/0293872 A1 | 12/2007 | Peyman |
| 2008/0077071 A1 | 3/2008 | Yaron et al. |
| 2008/0077238 A1 | 3/2008 | Deacon et al. |
| 2008/0200860 A1 | 8/2008 | Tu et al. |

FOREIGN PATENT DOCUMENTS

| | | |
|---|---|---|
| FR | 2233028 A1 | 1/1975 |
| GB | 2101891 A | 1/1983 |
| GB | 2160778 A | 1/1986 |
| GB | 2187963 A | 9/1987 |
| SU | 906561 A1 | 2/1982 |
| WO | 9112037 A1 | 8/1991 |
| WO | 9112046 A1 | 8/1991 |
| WO | 9118568 A1 | 12/1991 |
| WO | 9320783 A1 | 10/1993 |
| WO | 9402081 A1 | 2/1994 |
| WO | 2006012009 A2 | 2/2006 |
| WO | 2007087061 A2 | 8/2007 |

OTHER PUBLICATIONS

French Scale and Needle Gauge Cross Chart, Harvard Apparatus. Retrieved on May 7, 2014, Retrieved from the Internet:.

International Search Report and Written Opinion, mailed Feb. 26, 2010, and International Preliminary Report on Patentability, mailed May 10, 2011, for Application No. PCT/US2009/063332, 12 pages.

Kakaday T., et al., "Advances in Telemetric Continuous Intraocular Pressure Assessment," British Journal of Ophthalmology, 2009, vol. 93 (8), pp. 992-996.

Krupin T., et al., "Filtering Valve Implant Surgery for Eyes with Neovascular Glaucoma," American Journal of Ophthalmology, 1980, vol. 89 (3), pp. 338-343.

Lee P., et al., "Aqueous-Venous Shunt for Glaucoma. A Further Report," Archieves of Ophthalmology, 1981, vol. 99 (11), pp. 2007-2012.

Mokwa W., "Ophthalmic Implants," Sensors, Proceedings of IEEE, 2003, vol. 2, pp. 980-986.

Molteno A.C., "Use of Molteno Implants to Treat Secondary Glaucoma," 1986, pp. 211-238.

\* cited by examiner

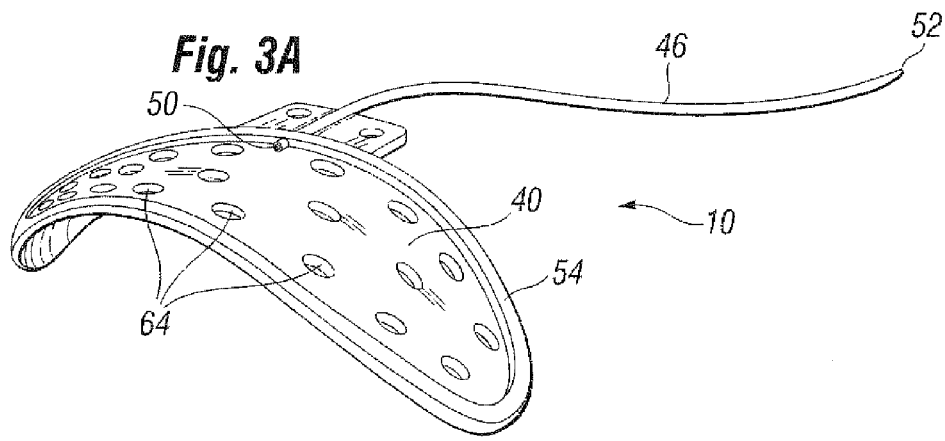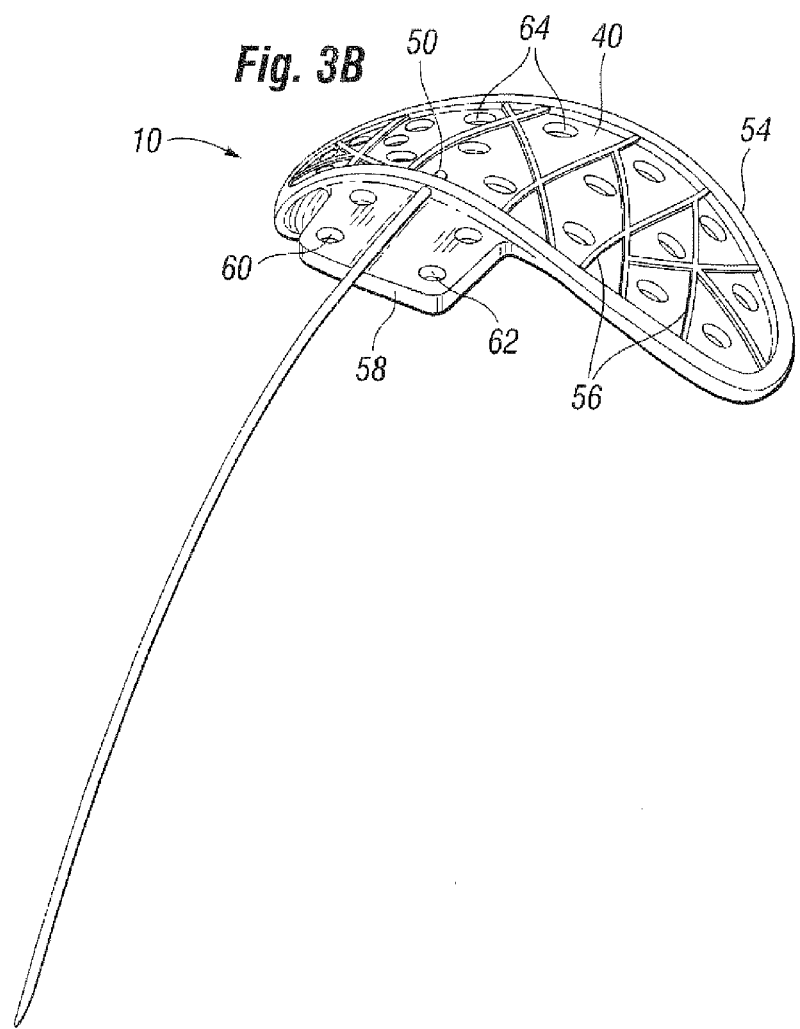

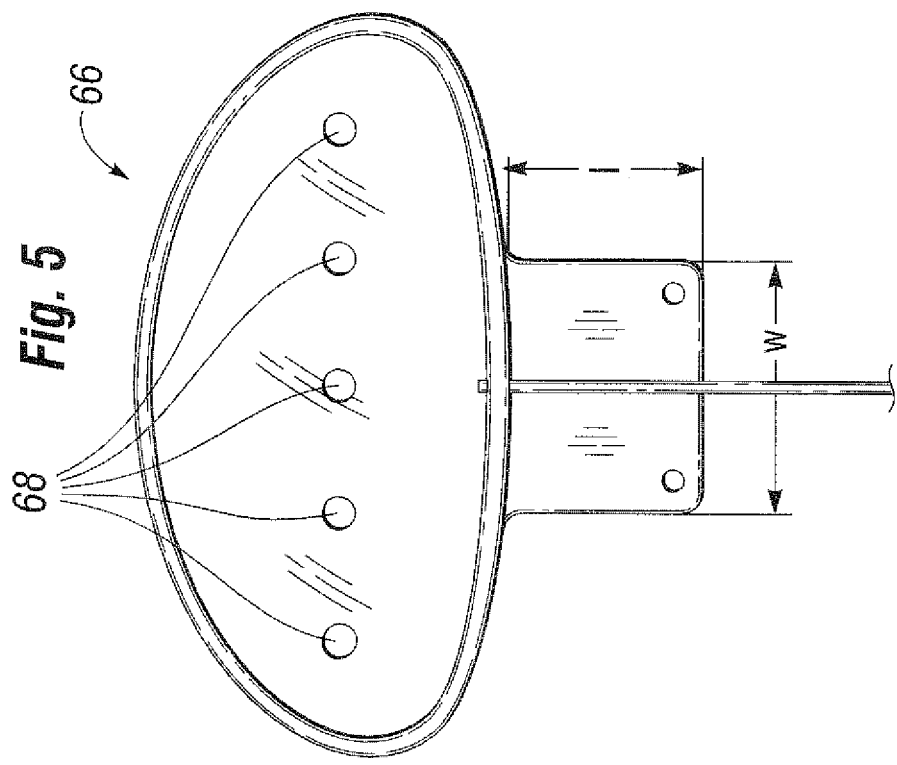
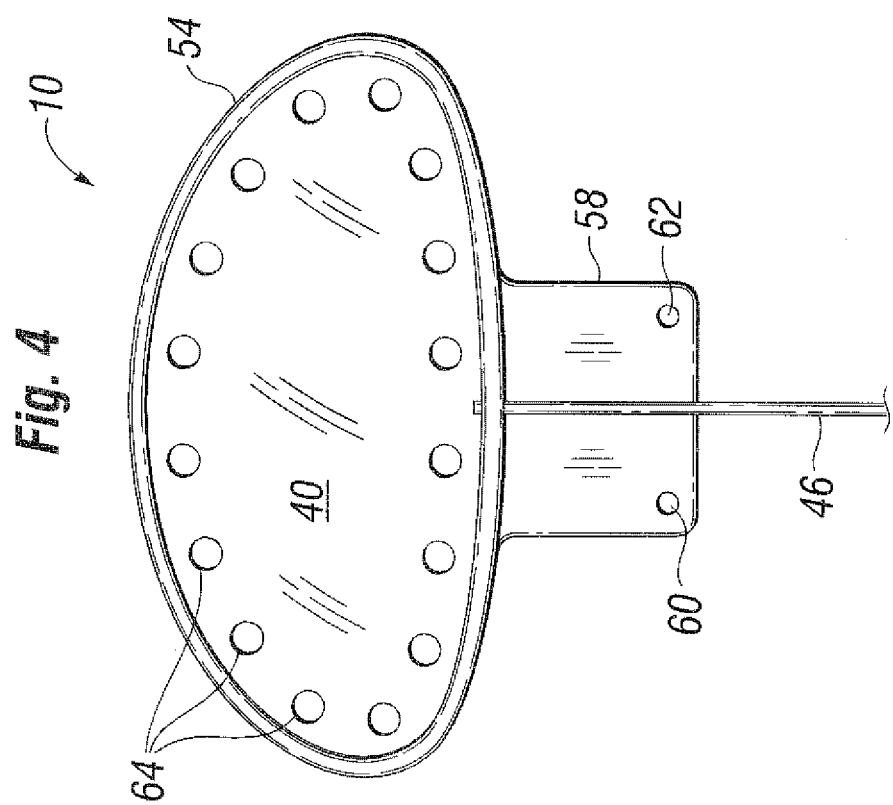

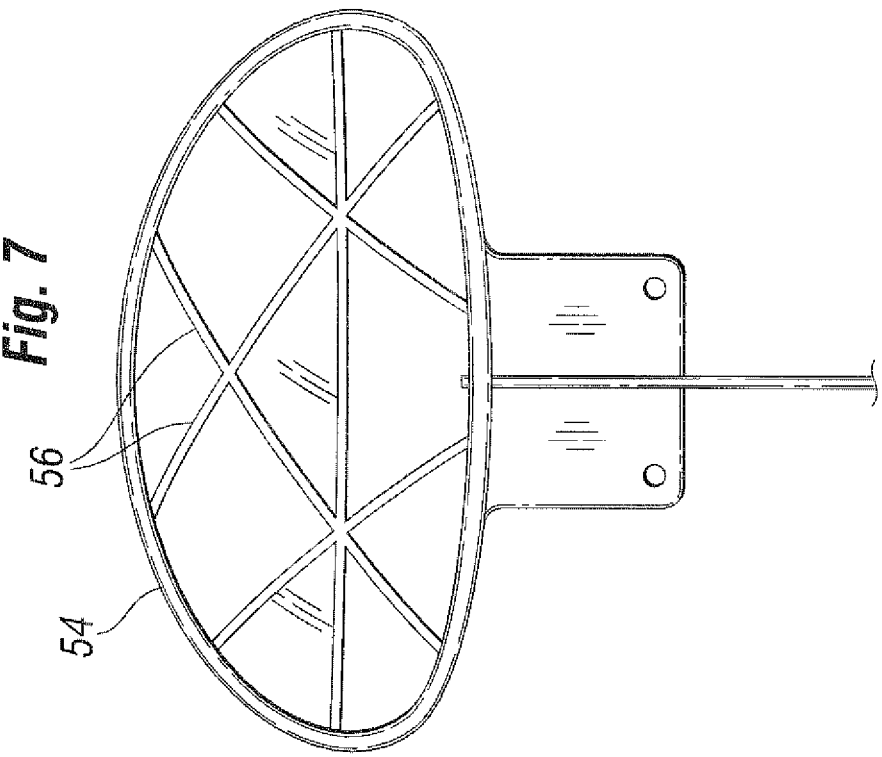
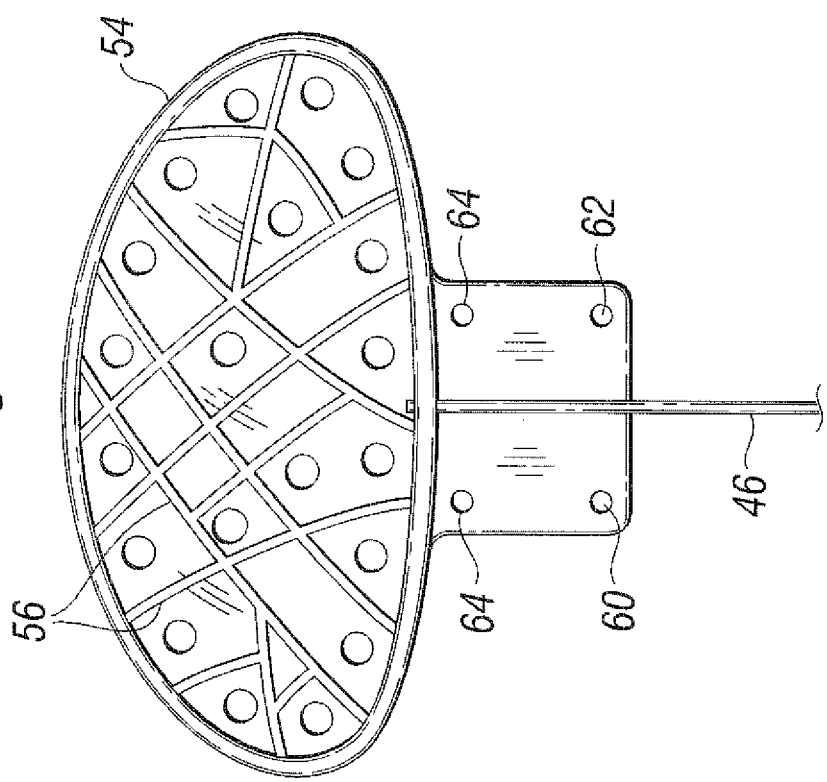

GLAUCOMA DRAINAGE SHUNTS AND METHODS OF USE

This application is a divisional application of and claims priority to U.S. application Ser. No. 13/714,050, entitled "GLAUCOMA DRAINAGE SHUNTS AND METHODS OF USE", filed on Dec. 13, 2012, which is a divisional application and claims priority to U.S. application Ser. No. 12/265,145, now U.S. Pat. No. 8,353,856, entitled "GLAUCOMA DRAINAGE SHUNTS AND METHODS OF USE", filed on Nov. 5, 2008, the entire contents of which are hereby incorporated by reference in their entirety for all purposes as if fully set forth herein.

FIELD OF THE INVENTION

The present invention relates to treatments for glaucoma in the eye and, more particularly, to glaucoma shunts and methods of use for draining fluid from the eye at a controlled rate.

BACKGROUND OF THE INVENTION

Intraocular pressure in the eye is maintained by the formation and drainage of aqueous, a clear, colorless fluid that fills the anterior and posterior chambers of the eye. Aqueous normally flows from the anterior chamber of the eye out through an aqueous outflow channel at a rate of 2 to 3 microliters per minute.

Glaucoma is a progressive disease of the eye characterized by a gradual increase of intraocular pressure. This increase in pressure is most commonly caused by stenosis or blockage of the aqueous outflow channel, resulting in excessive buildup of aqueous fluid in the eyeball. Other causes include increase in venous pressure outside the eye which is reflected back through the aqueous drainage channels and increased production of aqueous. In a "normal" eye, intraocular pressure ranges from 8 to 21 mm mercury. In an eye with glaucoma, intraocular pressure can range between normal pressures up to as much as 50 mm mercury. This increase in intraocular pressure produces gradual and permanent loss of vision in the afflicted eye.

Existing corrective methods for the treatment of glaucoma include drugs, surgery, and implants. Pharmacological treatment is prohibitively expensive to a large majority of glaucoma patients. In addition, many people afflicted with the disease live in remote or undeveloped remote areas where the drugs are not readily accessible. The drugs used in the treatment, in particular steroids, often have undesirable side effects and many of the long-term effects resulting from prolonged use are not yet known.

Surgical procedures have been developed in an effort to treat victims of glaucoma. An iridectomy, removal of a portion of the iris, is often used in angle-closure glaucoma wherein there is an occlusion of the trabecular meshwork by iris contact. Removal of a piece of the iris then gives the aqueous free passage from the posterior to the anterior chambers in the eye. A trabeculotomy, opening the inner wall of Schlemm's canal, is often performed in cases of developmental or juvenile glaucoma so as to increase the outflow of the aqueous, thereby decreasing intraocular pressure. In adults, a trabeculectomy shunts fluid through a trap-door flap in the eye that performs a valve-like function for the first few weeks after surgery.

While often successful, these surgical techniques possess inherent risks associated with invasive surgery on an already afflicted eye. Furthermore, the tissue of the eye can scar over this small area and the eye reverts to the pre-operative condition, thereby necessitating the need for further treatment.

Ocular implants are often used in long-term glaucoma treatment. One early implant is described in the paper entitled "Use of Molteno Implants to Treat Secondary Glaucoma" by A. C. B. Molteno and published by Grune & Stratton, Ltd, 1986, pp 211-238. The implant was a small circular plate with a rigid translimbal drainage tube attached thereto. The plate was 8.5 mm in diameter and formed a surface area of about 100 $mm^2$. This early Molteno implant was sutured to the sclera in the anterior segment of the eye at the limbus and the drainage tube was inserted into the anterior chamber of the eye. Once implanted, the body forms scar tissue around this plate. Fluid causes the tissues above the plate to lift and form a bleb into which aqueous flows from the anterior chamber via the drainage tube. A bleb is a fluid filled space surrounded by scar tissue.

Many problems occurred with the early Molteno device. The bleb that formed on the sclera was elevated, which resulted in Dellen formation (sterile corneal ulcers). The implant sometimes had to be removed in another surgery to cure the ulcers. Further, this early device often did not reduce the intraocular pressure enough to treat the glaucoma without the use of additional medications.

Dr. Molteno redesigned his implant for insertion into the posterior segment of the eye to avoid the problems with his early anterior device, as disclosed in U.S. Pat. No. 4,457,757 entitled "Device for Draining Aqueous Humor." This implant is commercially available as the Molteno® Seton Implant and is also referred to as the long tube Molteno implant. The implant comprises a flexible drainage tube connected to one or more rigid plate reservoirs, The plates are shaped to conform to the curvature of the eye. The long tube Molteno implant is disadvantageous as the plates are formed of a rigid plastic which makes insertion beneath the eye tissue difficult and time-consuming. The reservoir plate is placed under Tenon's capsule in the posterior segment of the eye and sutured to the sclera. The drainage tube is implanted into the anterior chamber through a scleral incision.

After a glaucoma implant is attached, intraocular pressure tends to fall as aqueous fluid flows immediately through the drainage tube. An open drainage tube may release too much of the fluid too fast, which is detrimental to the eye. It is not until 2-6 weeks later that the bleb forms to sufficiently regulate the fluid flow. Some prior devices have incorporated valves in the fluid drain path designed to function for a limited time until the bleb forms. However, such valved devices sometimes clog later, requiring another surgery.

More recently, U.S. Pat. Nos. 5,476,445 and 6,050,970 to Dr. George Baerveldt, et al. disclose glaucoma implants or shunts that include a flexible plate that attaches to the sclera and positions a drainage tube for insertion into the anterior chamber of the eye. A bleb forms around the plate and fluid drains into the bleb to regulate intraocular pressure. This type of shunt is sold as the Baerveldt® series of glaucoma implants by Advanced. Medical Optics (AMO) of Santa Ana, Calif. The Baerveldt® device has an open tube with no flow restricting elements. Temporary sutures are used to restrict fluid flow for a predetermined period after which the bleb forms and fluid drainage is properly regulated. The temporary sutures are either biodegradable or removed in a separate procedure. This method works mostly, but the timing of suture dissolution is necessarily inexact and a second procedure undesirable. The Baerveldt® shunts also include four fenestrations to promote fibrous adhesion, which may reduce bleb height.

Despite accepted treatments for regulation of intraocular pressure using glaucoma shunts, there is a need for an implant that does not require temporary sutures.

BRIEF SUMMARY OF THE INVENTION

According to one aspect of the inventions disclosed herein, a glaucoma drainage device is described along with methods of implantation that allow for controlled outflow of aqueous fluid to assist in reducing heightened intraocular pressure associated with glaucoma. In various embodiments, the drainage device includes a plate and a drainage tube having an open cross-section and connected to the plate such that an outflow end of the drainage tube connects to a part of the plate and an inflow end of the drainage tube extends away from the plate. The inflow end of the drainage tube is configured to be inserted through an incision at or near the limbus of an eye and into the anterior chamber of the eye, with the hoop strength of the drainage tube chosen such that the tube wall assumes a collapsed shape within the incision after insertion due to the pressure of the incision walls and/or a relatively sharp angle of insertion of the tube. The resiliency of the drainage tube is such that the tube wall will resiliently expand from its collapsed shape to its open cross-section within the incision after a predetermined time after implant. This results in a flow restrictor wherein the drainage tube gradually opens over time to allow for greater outflow of fluid.

According to further aspects of the inventions disclosed herein, methods of implanting such glaucoma drainage devices are disclosed wherein the drainage device plate is typically positioned beneath Tenon's capsule and a portion of the rectus muscle. The drainage tube is then inserted through an incision in the region of the limbus such that the inflow end of the tube extends into the anterior chamber of the eye. Desirably, the tube is inserted at a relatively sharp angle through the limbus incision, and optionally a dissolving holding suture may be used to help kink the tube at the incision. The relatively sharp entry angle of the drainage tube and/or the initial pressure from the incision walls assists in collapsing the drainage tube which acts as a flow restrictor. The drainage tube possesses sufficient resiliency or hoop strength to restore patency of the tube over time such that outflow increases over time.

These and other advantages of these embodiments will become apparent to those skilled in the art from the following detailed description of the invention and the accompanying drawings.

BRIEF DESCRIPTION OF THE DRAWINGS

Features and advantages of the present invention will become appreciated as the same become better understood with reference to the specification, claims, and appended drawings wherein:

FIG. 3A is a first perspective view of an exemplary glaucoma shunt of the present invention from the plate side;

FIG. 3B is a second perspective view of the exemplary glaucoma shunt from the drainage tube side;

FIG. 4 is a plan view of the exemplary glaucoma shunt of the present invention;

FIG. 5 is a plan view of an alternative glaucoma shunt of the present invention without fenestrations; and FIGS. 6 and 7 are plan views of alternative glaucoma shunts of the present invention.

DETAILED DESCRIPTION OF THE PREFERRED EMBODIMENTS

Figure 1:
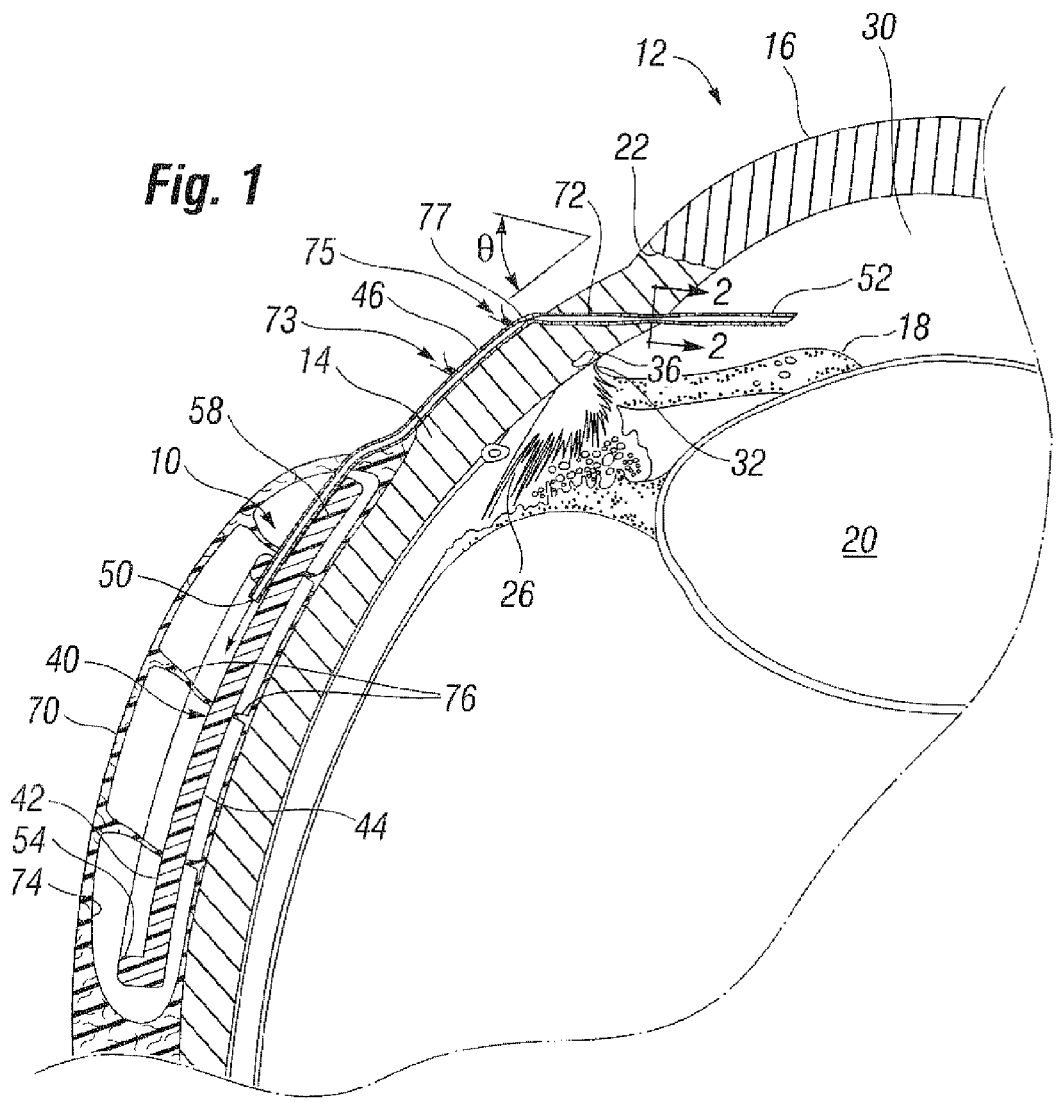
FIG. 1 is a cross-sectional view of the human eye which illustrates the glaucoma shunt of the present invention after implant.

FIG. 1 illustrates a glaucoma shunt 10 constructed in accordance with the present invention positioned within the tissue of an eye 12. The relevant structure of the eye 12 will be described briefly below to provide background for the anatomical terms incorporated herein, however, it should be realized that several anatomical details have been omitted for clarity of understanding. The tough outer membrane known as the sclera 14 covers all of the eye 12 except that portion covered by the cornea 16, the thin, transparent membrane which enables light to enter the pupil 18 and the iris aperture in front of the lens 20. The cornea 16 merges into the sclera 14 at a juncture referred to as the sulcus of the sclera or as the limbus 22. The ciliary body 26 begins at the limbus 22 and extends along the interior of the sclera 14.

It is well-known that aqueous is produced by the ciliary body 26 and reaches the anterior chamber 30 formed between the iris 18 and the cornea 16 through the pupil 20. In a normal eye, the aqueous is removed through the trabecular meshwork 32. There the aqueous passes through Schlemm's canal 36 and through veins which merge with blood-carrying veins and into venous circulation. Intraocular pressure is maintained in the eye 12 by the intricate balance of secretion and absorption or outflow of the aqueous in the manner described above. Glaucoma results from excessive buildup of aqueous fluid in the anterior chamber 30 which produces an increase in intraocular pressure. The present invention is designed for treatment of glaucoma by facilitating the outflow of the aqueous from the anterior chamber 30 of the eye 12.

The glaucoma shunt 10 comprises a pliable plate 40, also referred to as a pliable seton in the ophthalmic field, having oppositely disposed convex outer 42 and concave inner 44 curved surfaces. The plate 40 conforms to the sclera 14 and connects to a discharge or drainage tube 46 that extends into the anterior chamber 30 of the eye 12.

The plate 40 is preferably formed of silicone elastomer, such as SILASTIC®, Medical Grade Q7-4765, 65 Shore A, manufactured by Dow Corning Corporation of Midland, Mich. or Nusil Corp. of Santa Barbara, Calif., although other silicone elastomers in the range of 40-85 Shore A and having good elastic memory are also suitable. The silicone elastomer is filled with a radiopaque material, such as Barium Sulfate, so that the implant is visible in X-rays procedures.

With reference now to FIGS. 3A, 3B and 4, elements of the glaucoma shunt 10 can be more clearly described. The drainage tube 46 comprises an outflow end 50 and an inflow end 52, wherein the outflow end 50 attaches to the plate 40. The plate 40 has a generally spherical curvature with an elliptical perimeter looking down or in plan view, as in FIG. 4. The surface area of the plate 40 is preferably in the range of approximately 100 to 600 mm$^2$ depending on glaucoma conditions and the radius of curvature of the plate 40 is preferably 12-14 mm. A raised ridge 54 projects outward from the outer convex surface 42 and extends around the perimetric edge of the plate 40. The inner surface 44 of the plate 40 curves to conform to the curvature of the eye 12, specifically the curvature of the sclera 14, and the ridge 54 follows that curvature. A plurality of cross beams 56 (FIGS. 3B and 5) for structural strength may also be provided traversing the plate 40 and connecting to the ridge 54 around the periphery, and to each other. The cross beams 56 may have the same thickness as the ridge 54 or be somewhat thinner.

The thickness of the plate 40 is preferably in the range of about 0.5 to 3.0 mm, and in an exemplary embodiment is about 0.94 mm. The thickness of the plate 40 and ridge 54 is desirably about 150-200% the thickness of the plate itself. The peripheral ridge 54 provides rigidity to the plate 40 to assist a surgeon to manipulate it through an incision and into proper placement. Moreover, the structural strength provided by the peripheral ridge 54 permits the central portion of the plate 40 to be made thinner, potentially 0.2 mm or 0.25 mm thinner than previous designs, or 10-50% thinner or more in relative terms. A thinner plate 40 forms a thinner bleb, which assists in the eventual pressure regulating function of the shunt 10. That is, a thicker bleb wall is typically associated with a higher IOP in the eye. Conversely, reducing the bleb thickness increases outflow, which in turn decreases the ocular IOP. The precisely engineered plate 10 then governs the increased outflow of aqueous fluid.

The drainage tube 46 connects to the plate 40 with adhesive, such as Clear Silicone Rubber Adhesive RTV-118 manufactured by General Electric Silicone Products of Waterford, N.Y., via a small hole formed in the ridge 54. The outflow end 50 of the tube 46 open to and thus drains into the shallow outer recess bordered by the ridge 54 and over the smooth outer surface 42 of the plate 40.

The drainage tube 46 is preferably about 5 mm to 35 mm in length, formed of SILASTIC®, Medical Grade RX-50, also available from Dow Corning Corporation or Nusil Corp. of Santa Barbara. In addition to Silicone, Teflon or polyurethane are also materials that may be suitable for the tube 46. The present invention contemplates an extremely thin tube 46 that functions as a temporary flow restrictor to stem the loss of aqueous fluid prior to proper formation of a bleb, as described below. In one embodiment, the tube 46 has an outside diameter (OD) of less than about 0.50 mm, with an inside diameter (ID) typically less than about 0.25 mm. The wall thickness is desirably 0.125 mm or less, and more desirably 0.124 mm or less. For example, the wall thickness may be 0.12 mm or 0.10 mm or less. The small cross-section of the tube 46 enables it to collapse when inserted in the incision through the limbus 22 and therefore prevent fluid flow between the tube ends 50, 52. In this regard, the salient property of the tube is its hoop strength/compressibility, or ability to withstand collapse.

Those of skill in the art will understand that the exemplary dimensions given above may be modified for different materials to produce the same desired hoop strength. The tube 46 must be compressible to collapse when inserted through the cornea, sclera, or limbus tissue, but must also be able to rebound to restore patency. The process is described below. It should also be noted that prior art drainage tubes were constructed considerably larger and were too stiff to be collapsed only by the pressure of the incision itself. In one exemplary prior art device the drainage tube had an OD of 0.60 mm, an ID of 0.30 mm, and a wall thickness of 0.15 mm, which was too stiff to effectively collapse and restrict flow.

The edges of the plate 40 are desirably radiused, tapered and blended so as to facilitate insertion. Additionally, the rounded edge of the plate 40 discourages scar tissue around the edge of the plate 40. The rounded edge of the plate 40 also presents a smooth surface to decrease tissue irritation.

A tab or extension 58 of the shunt 10 formed adjacent the ridge 54 extends from one long side of the plate 40 and includes two suture holes 60, 62 at an edge farthest from the plate. The extension 58 is desirably larger in size than previous such tabs to facilitate implant. That is, the plate 40 can be positioned relatively far back around the eye 12 with the suture holes 60, 62 on the extension 58 plainly visible and accessible. In a preferred embodiment, the plate 40 attaches to the sclera such that the ridge 54, and thus the outflow end 50 of the drainage tube 46, is located between about 8-12 mm posteriorly from the limbus 22. To permit this desirable positioning, the extension 58 has a width w between about 4 mm and about 12 mm, and desirably between about 4 mm and about 8 mm, and a length l between about 2 mm and about 10 mm, and desirably between about 4 mm and about 8 mm, as seen in an alternative shunt 66 of FIG. 5. The shunt 66 also includes fewer fenestrations 64 like shunts of the prior art.

The plate 40 of the embodiment of FIGS. 3-4 includes a series of holes or fenestrations 64 from the outer surface 42 to the inner surface 44. The fenestrations 64 permit aqueous fluid to pass from one side of the plate 40 to the other. In a preferred embodiment there are 16 fenestrations 64 spaced evenly around the periphery of the plate 40 just inside the ridge 54.

FIGS. 6 and 7 are plan views of alternative glaucoma shunts of the present invention. These views illustrate possible configurations of the cross beams 56 as well as fenstrations 64. It should be noted here that the shunts, and in particular the cross beams 56, may be structurally strengthened by first impregnating them with barium during fabrication, and then irradiating them with gamma rays. This process will increase polymer cross-linkages in the material and thus increase strength.

The present invention can be implanted using known ophthalmological surgical techniques and, with reference to FIG. 1, the surgical implant procedure will be briefly described. An initial incision is made in the Tenon's capsule 70 parallel to the limbus 22. The plate 40 is inserted through the initial incision and positioned beneath the Tenon's capsule 70 and a portion of the rectus muscle (not shown) or extending totally under one or more muscles, thus covering the sclera 14. The plate 40 can be sutured to the sclera 14, or alternatively, to the rectus muscle if the sclera 14 is thinned by disease, with the suture holes 60, 62. Preferably, non-absorbable nylon sutures are used in the suture holes 60, 62 to secure the plate 40, such as 8-O nylon or polypropylene sutures.

The drainage tube 46 tunnels out through the sclera 14 and the cornea 16 beneath Tenon's capsule 70 and in through an incision 72 in the region of the limbus 22 such that the inflow end 52 of the tube 46 extends into the anterior chamber 30 of the eye 12. A suture is typically used inside the tube as a stent to maintain stiffness during insertion. A dissolvable holding suture 73 secures the tube 46 to the exterior of the sclera. Desirably, a relatively sharp bend angle θ of between about 10-90° forms in the tube 46 just before entering the incision 72. The bend angle θ is formed at a kink 77 in the tube 46 that will be discussed in greater detail below. An optional dissolvable or removable kinking suture 75 may facilitate formation of the kink 77, although it should be understood that the inherent pliability of the tube 46 obviates the need for such a suture. The exposed portion of the drainage tube 46 is then typically covered with a scleral reinforcing element (not shown), such as a connective tissue graft, i.e., a sclera graft, dura mater graft, fascia lata graft, or a graft formed from other biocompatible materials.

A large drainage bleb 74 eventually surrounds the plate 40 and lifts the layer of Tenon's capsule 70 above the sclera 14. The plate acts as a permanent bleb controlling stent to inhibit the tendency of the body to heal itself which would eliminate the bleb. Fibrous rivets of sear tissue 76 form on both sides of the plate 40, causing a low bleb.

As mentioned, the tube 46 and method of insertion are designed to initially restrict fluid flow after implant, but gradually permit flow. There are two ways flow restriction is contemplated: the tube 46 may collapse under pressure of the walls of the incision 72, or a sharp bend angle may be created at the kink 77 which closes the tube lumen. Either or both of these solutions may be utilized and are described below.

Figure 2A:
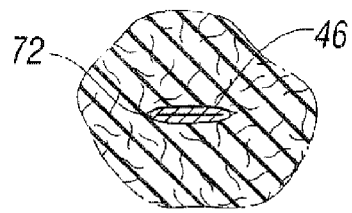
FIG. 2A is a detailed sectional view through the corneal/scleral tissue showing a flattened profile of the drainage tube just after insertion through the incision.
Figure 2B:
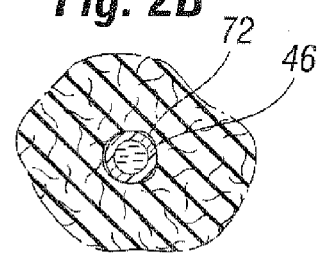
FIG. 2B is a sectional view through the corneal/scleral tissue showing the patent profile of the drainage tube several weeks after implant.

FIG. 2A shows the tube 46 after having been inserted through the incision 72. The pressure of the incision walls collapses the tube 46, as mentioned above. The tube 46 possesses sufficient resiliency to eventually push outward against the incision walls as seen in FIG. 2B and restore patency to the tube 46. This transition is assisted at all times by internal aqueous fluid pressure from the eye 12 in the portion of the tube lumen leading to the anterior chamber 30. Furthermore, the presence of aqueous fluid "wets" the tube and the output fluid pressure assists the process of opening the tube. Therefore, the combined forces of the internal fluid pressure and inherent resiliency of the wall of the tube 46 work against the inward pressure of the incision walls. As the latter inward force gradually diminishes, from a tissue indentation effect described below, the tube 46 gradually opens.

FIG. 1 shows the relatively sharp bend angle θ at the kink 77. The lumen of the tube 4 6 closes or collapses—either completely or substantially—at the kink 77, thus restricting flow through the tube 46. A substantially closed or collapsed lumen is one that closes to an opening having a cross-sectional area that is less than about 25% of that of the fully open lumen, or desirably closes to less than about 10% of the fully open lumen or less. Eventually, some time after implant and in a similar manner as the recovery of the collapsed portion of the tube 46, internal aqueous fluid pressure from the eye 12 in conjunction with the tube becoming "wetted" causes the kink to resiliently assume an arc, therefore opening its lumen. If the optional kinking suture 75 is used it may dissolve or be removed to help speed opening of the kink 77.

This system thus functions as a flow restrictor to initially restrict and gradually permit flow through the tube 46, though no temporary sutures are used and there is no need for a follow-up procedure. Desirably the tube 46 remains closed or mostly closed until the bleb 74 has formed, so that aqueous fluid does not drain too fast from the anterior chamber 30. In most cases the bleb forms within 2-6 weeks, which corresponds to the period during which the tube 46 remains at least partly closed. Once open, the tube 46 desirably permits fluid flow of around 2.4 microliters per minute.

The phenomena believed responsible for the change in tube profile after implant is slow deformation (rounding) of the incision tissue or wound. The incision begins as two flat surfaces which compress the tube 46 essentially flat. Much like the imprint left on ones finger from wearing a ring, the incision tissue eventually begins to lose elasticity and succumb to the outward pressure from the tube, and begins to relax and form a tissue indentation from the tube. If the tube 46 were removed in the situation seen in FIG. 2B, the tissue indent would remain, at least for a time, such that the incision is somewhat rounded. The invention contemplates a wide range of tube materials and sizes to function as a temporary flow restrictor in this manner, and appropriate testing will validate a number of combinations.

The self-regulating feature of the glaucoma shunt 10 as described herein eliminates the need for temporary sutures and follow-up procedures. This greatly decreases the amount of complications, and the small size of the tube 46 reduces incidences of corneal irritation and potential complications.

While the invention has been described in its preferred embodiments, it is to be understood that the words which have been used are words of description and not of limitation. Therefore, changes may be made within the appended claims without departing from the true scope of the invention.

What is claimed is:

1. A method of treating glaucoma in an eye utilizing an implanted drainage device, the method comprising the steps of:
   providing a glaucoma shunt comprising a plate and an elastomeric drainage tube having an open cross-section, an outflow end of the elastomeric drainage tube connected to a part of the plate and an inflow end extending away from the plate, the drainage tube having an open lumen and a tube wall with a hoop strength;
   positioning the glaucoma shunt in the eye with the plate positioned on the sclera posterior to the limbus;
   forming an incision at or near the limbus; inserting the inflow end of the drainage tube through the incision and the inflow end into the anterior chamber of the eye;
   bending the drainage tube to extend along the sclera close to the incision to create a kink in the drainage tube as it enters the incision, the kink restricting flow through the open lumen;
   securing the drainage tube to the sclera with a kinking suture close to the incision to facilitate formation of the kink;
   wherein the kinking suture creates a sharp bend angle in the tube, and the sharp bend is spaced a distance from the kinking suture;
   leaving the glaucoma shunt in place for a sufficient amount of time to permit formation of a scar tissue bleb around the plate; and
   causing removal of the kinking suture to permit the drainage tube to resiliently expand to permit fluid flow therethrough.

2. The method of claim 1, wherein the drainage tube is inserted into the incision at a bend angle of between about 10 degrees and about 90 degrees.

* * * * *